United States Patent [19]

Cimber

[11] Patent Number: 4,715,365
[45] Date of Patent: Dec. 29, 1987

[54] INTRAUTERINE CONTRACEPTIVE DEVICE

[76] Inventor: Hugo Cimber, Neufeldstrasse 134, 3012 Bern, Switzerland

[21] Appl. No.: 883,183

[22] Filed: Jul. 8, 1986

[30] Foreign Application Priority Data

Jul. 11, 1985 [CH] Switzerland .................. 3015/85

[51] Int. Cl.⁴ ............................................. A61F 5/46
[52] U.S. Cl. ................................................. 128/130
[58] Field of Search .............................. 128/127–131; 604/15–17

[56] References Cited

U.S. PATENT DOCUMENTS

| | | | |
|---|---|---|---|
| 3,507,274 | 4/1970 | Soichet | 128/130 |
| 3,678,927 | 7/1972 | Soichet | 128/130 |
| 3,811,435 | 5/1974 | Soichet | 128/130 |
| 3,935,860 | 2/1976 | Hoff | 128/130 |

FOREIGN PATENT DOCUMENTS 505617  5/1971  Switzerland .

Primary Examiner—James R. Feyrer
Assistant Examiner—Danton D. DeMille
Attorney, Agent, or Firm—Townsend and Townsend

[57] ABSTRACT

The device is to be introduced into the uterus by means of a tube. It comprises two branches linked to the front end of a support rod, which branches spread apart upon expulsion of the support rod from the tube. Each of the branches bears at its free end a soft, pear-shaped terminal member and comprises a comparatively rigid positioning part. The terminal member is secured to a thin, flexible and movable prolongation at the end of the branch.

8 Claims, 1 Drawing Figure

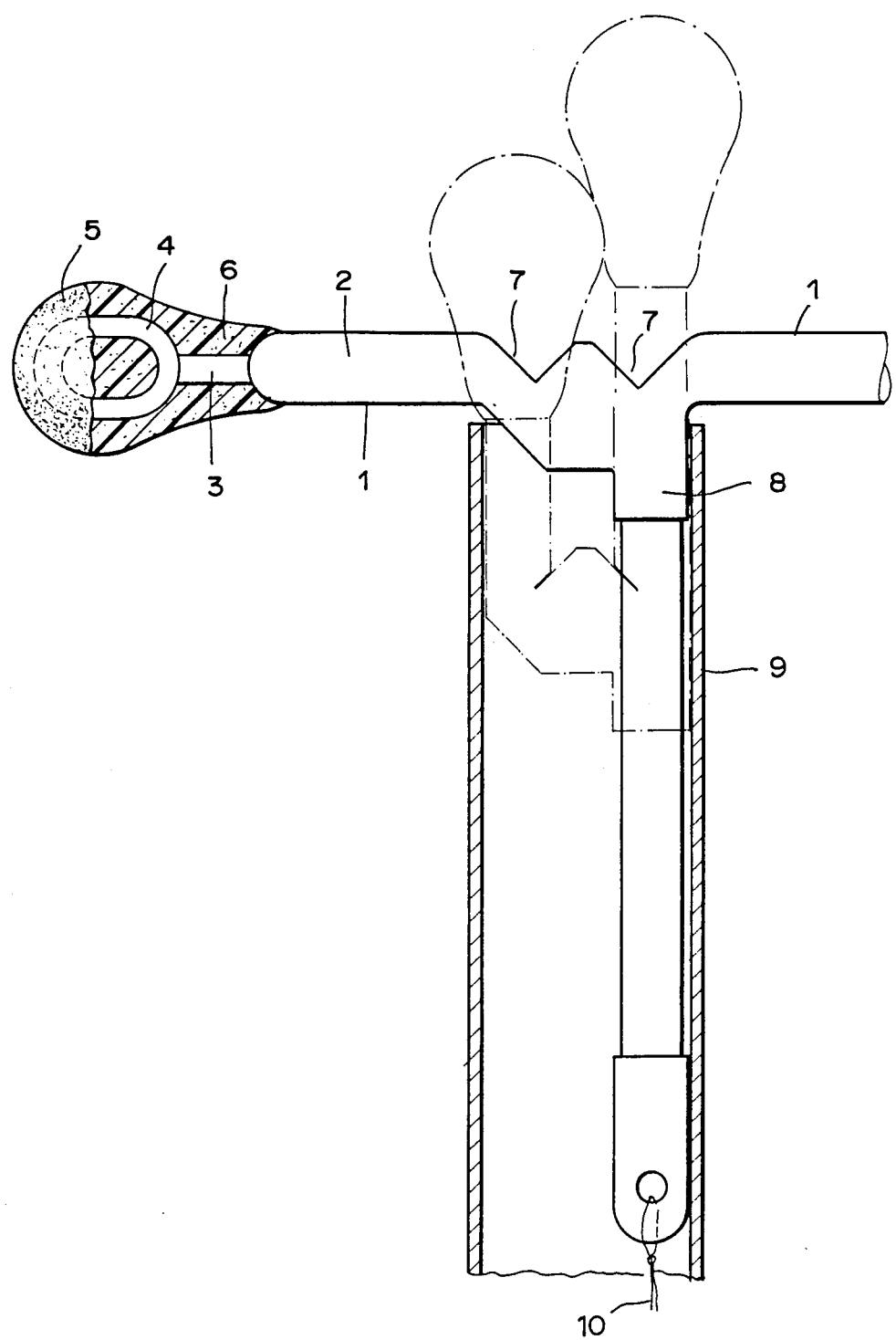

INTRAUTERINE CONTRACEPTIVE DEVICE

This invention relates to contraceptives, and more particularly to an intrauterine contraceptive device (IUD) to be introduced into the uterus by means of a tube, of the type having a support rod and two branches linked to the forward end thereof, in the direction of introduction, in such a way that after these branches have been expelled from the tube they spread apart laterally, each of the branches bearing at its free end a spherical terminal member, which terminal members are intended and suitable for closing the mouths of the Fallopian tubes opening into the uterus, each of the branches consisting of a comparatively rigid positioning part, as well as a soft terminal member.

The difficulty with IUDs of the above type is to bring the spherical terminal members with sufficient reliability to the location to be sealed off. Essentially, this is possible only if the branches are made comparatively rigid, whereas the terminal members affixed to the outer ends of these branches are themselves then joined by an extremely flexible connection to these rigid branches.

It is an object of this invention to provide an improved IUD by means of which the terminal members can be more reliably conveyed to the location to be sealed off.

To this end, in the intrauterine contraceptive device according to the present invention, of the type initially mentioned, the terminal members are affixed to a thin, flexible and movable prolongation at the free end of each branch, the prolongations serving not only to connect the positioning parts to a terminal member, but at the same time also to hold an apertured localizing part.

A preferred embodiment of the invention will now be described in detail with reference to the accompanying drawing, which is a partial section on a larger scale through one of the laterally projecting branches in its expelled state.

In the embodiment illustrated, the branches 1 are made in two pieces and each comprise a positioning part 2, adjacent to which there is a thin, flexible and, as such, movable prolongation 3 which connects positioning part 2 to an apertured, eyelet-shaped supporting part 4.

Supporting part 4, the purpose of which is to improve the positioning possibility with the aid of ultrasonic waves, may be of any shape favorable for anchoring provided it has at least one aperture for the purpose of being made visible through ultrasonic waves. In the embodiment shown, supporting part 4 is annular. Affixed to supporting part 4 is the outer covering of a pear-shaped terminal member 5, the attachment portion 6 of which surrounds prolongation 3 and is affixed to the end of positioning part 2, which may be of any rigid material, preferably a suitable plastic, and has on the top two notches 7 which produce a cross-sectional weakening at that location. The shape is such that the pear-shaped terminal members 5, together with the respective attachment portions 6, form a pear-shaped body. Rigid positioning part 2 presses the soft terminal member 5 against the wall of the uterus and thus brings about the fixing of the entire IUD in the uterus without any danger of perforating the uterine wall. The rigidity of positioning parts 2 may be increased to the maximum, which can prevent spontaneous expulsion of the IUD from the uterus.

Thus, when a support rod 8, preferably wound with copper wire (not shown), is expelled together with its branches 1 from an insertion tube 9, as is customary with IUDs of this kind, branches 1 spread apart in opposite directions. The dimensions are such that the ejected branches 1 are directed at least approximately toward the openings of the Fallopian tubes into the uterus. Owing to their shape, the soft terminal members 5, flexibly connected to positioning parts 2, then reach precisely the location to be sealed off, even if the direction of positioning parts 2 should not be quite exact.

Therefore, though positioning parts 22 might not be absolutely aimed at the mouths of the Fallopian tubes opening into the uterus, sealing-off of the respective mouths is ensured by means of the arrangement described, especially by the flexible connection between the positioning parts 2 and the pear-shaped terminal members 5.

To remove the IUD from its operative position, it suffices to pull support rod 8 downward by means of a retraction means 10 so that the two branches 1 move back toward one another. Inasmuch as the branch 1 illustrated already bends at the location of the cross-sectional weakening formed by outer notches 7, whereas bending of the other branch 1 takes place only in proximity to support rod 8, the two pear-shaped terminal members 5 at the ends of the two branches 1 come to lie one below the other and thus fit within the inside diameter of insertion tube 9. This is facilitated by the pear-shape of terminal members 5 in that, as a result of the position of notches 7, the thicker end of one terminal member rests against the thinner neck of the other when the branches are not spread apart.

What is claimed is:

1. An intrauterine contraceptive device of the type to be introduced into and withdrawn from the uterus by a tube for closing the mouths of the Fallopian tubes, comprising:
   a support rod having an outer end;
   first and second branches extending laterally from the outer end of the support rod;
   the first and second branches including first and second pivots at which the respective branches pivot when entering and leaving the tube;
   the first and second branches having enlarged terminal members at the terminal ends of the branches for engagement with the mouths of the Fallopian tube; and
   the first and second pivots positioned at first and second distances from the outer end of the support rod, the second distance being substantially greater than the first distance so that when the first and second branches are housed within the tube the enlarged terminal members are axially displaced with the terminal end of the second branch lying behind the terminal end of the first branch.

2. The device of claim 1 wherein the first pivot includes a weakened region along the first branch.

3. The device of claim 2 wherein the weakened region is generally axially aligned with the support rod so that the first distance is about zero.

4. The device of claim 1 wherein the second pivot includes a weakened region along the second branch.

5. The device of claim 1 wherein the weakened region is a notched region.

6. The device of claim 1 wherein the terminal members are pear-shaped.

7. The device of claim 1 wherein the first and second branches each includes outer flexible portions and inner stiff portions, the outer flexible portions connecting the terminal members to the inner stiff portions, the outer flexible portions aiding engagement of the terminal members with the mouths of the Fallopian tubes.

8. An intrauterine contraceptive device of the type to be introduced into and withdrawn from the uterus by a tube for closing the mouths of the Fallopian tubes, comprising:

a support rod having an outer end;

first and second branches extending laterally from the outer end of the support rod, the first and second branches each including outer flexible portions and inner stiff portions;

the first and second branches including first and second weakened regions at which the respective branches pivot when entering and leaving the tube;

the first and second branches having enlarged terminal members, mounted to the outer flexible portions, for engagement with the mouths of the Fallopian tube, the outer flexible portions aiding engagement of the terminal members with the mouths of the Fallopian tubes; and the first and second weakened regions positioned at first and second distances from the outer end of the support rod, the second distance being substantially greater than the first distance so that when first and second branches are housed within the tube the enlarged terminal members are axially displaced with the terminal end of the second branch lying behind the terminal end of the first branch.

* * * * *